United States Patent
Hepp et al.

(10) Patent No.: US 10,101,285 B2
(45) Date of Patent: Oct. 16, 2018

(54) THERMAL FLOW SENSOR FOR DETERMINING A GAS OR THE COMPOSITION OF A GAS MIXTURE AS WELL AS ITS FLOW VELOCITY

(71) Applicant: Innovative Sensor Technology IST AG, Ebnat-Kappel (CH)

(72) Inventors: Christoph Hepp, Wil (CH); Florian Krogmann, Kreuzlingen (CH)

(73) Assignee: INNOVATIVE SENSOR TECHNOLOGY IST AG, Ebnat-kappel (CH)

( * ) Notice: Subject to any disclaimer, the term of this patent is extended or adjusted under 35 U.S.C. 154(b) by 471 days.

(21) Appl. No.: 14/773,802

(22) PCT Filed: Feb. 24, 2014

(86) PCT No.: PCT/EP2014/053533
§ 371 (c)(1),
(2) Date: Sep. 9, 2015

(87) PCT Pub. No.: WO2014/139786
PCT Pub. Date: Sep. 18, 2014

(65) Prior Publication Data
US 2016/0025660 A1 Jan. 28, 2016

(30) Foreign Application Priority Data
Mar. 11, 2013 (DE) .......................... 10 2013 102 398

(51) Int. Cl.
*G01N 25/00* (2006.01)
*G01F 1/68* (2006.01)
(Continued)

(52) U.S. Cl.
CPC .............. *G01N 25/00* (2013.01); *G01F 1/68* (2013.01); *G01F 1/692* (2013.01); *G01F 1/699* (2013.01); *G01N 33/0027* (2013.01)

(58) Field of Classification Search
CPC ...... G01N 25/00; G01N 33/0027; G01F 1/68; G01F 1/692; G01F 1/699
(Continued)

(56) References Cited

U.S. PATENT DOCUMENTS

| 5,117,691 A | 6/1992 | Fraser |
| 7,096,723 B2 | 8/2006 | Kienzle et al. |
(Continued)

FOREIGN PATENT DOCUMENTS

| DE | 10063752 A1 | 6/2002 |
| DE | 102007033144 A1 | 1/2009 |
(Continued)

OTHER PUBLICATIONS

English Translation of International Preliminary Report on Patentability, WIPO, Geneva, dated Sep. 24, 2015.
(Continued)

*Primary Examiner* — Daniel S Larkin
(74) *Attorney, Agent, or Firm* — Bacon & Thomas, PLLC

(57) ABSTRACT

A thermal flow sensor for determining a gas or the composition of a gas mixture as well as its flow velocity, comprising: a substrate onto which at least a first dielectric layer is applied; at least one heating structure that is applied onto the first dielectric layer and serves to heat the gas or the gas mixture; at least a first temperature sensor element that is applied onto the first dielectric layer at a distance from the heating structure and captures the temperature of the gas or gas mixture heated at the heating structure; a control device that controls the heating structure in a first operating mode in such a way that the heating structure shows a predetermined temperature, and controls the heating structure in a second operating mode in such a way that a power input into the heating structure corresponds to a predetermined power; and an evaluation unit which determines at least one physical characteristic of the gas present or the gas mixture on the basis of the operating modes and determines the gas present or the composition of the gas mixture as well as its flow velocity on the basis of this physical characteristic.

18 Claims, 3 Drawing Sheets

(51) Int. Cl.
*G01N 33/00* (2006.01)
*G01F 1/692* (2006.01)
*G01F 1/699* (2006.01)

(58) Field of Classification Search
USPC ....................................................... 73/25.05
See application file for complete search history.

(56) References Cited

U.S. PATENT DOCUMENTS

| 7,399,118 | B2 | 7/2008 | Matter et al. |
| 8,935,950 | B2 | 1/2015 | Bierl et al. |
| 2008/0034861 | A1 | 2/2008 | Bognar |

FOREIGN PATENT DOCUMENTS

| DE | 102010030952 A1 | 1/2012 |
| DE | 102011075519 A1 | 11/2012 |
| DE | 102011081923 A1 | 2/2013 |
| EP | 1391703 A1 | 2/2004 |

OTHER PUBLICATIONS

International Search Report,, EPO, The Netherlands, dated Jun. 3, 2014.
German Search Report, German PTO, Munich, dated Sep. 17, 2013.
"A Thermal Flow Sensor with Liquid Characterization Feature," Ali S. Cubukcu et al., Sensors 2010 Conference IEEE, 2010, pp. 2455-2459.
"Gas Concentration and Flow Speed Measurements using a Polymer-based Membrane Sensor," C. Hepp et al., 2013 IEEE Sensors, IEEE, Nov. 3, 2013, pp. 1-4.
"Micromachined flow sensors—a review," N. T. Nguyen, Flow Measurement and Instrumentation, Butterworth-Weinemann, Oxford, Great Britain, vol. 8, No. 1, Mar. 1997, pp. 1-10.

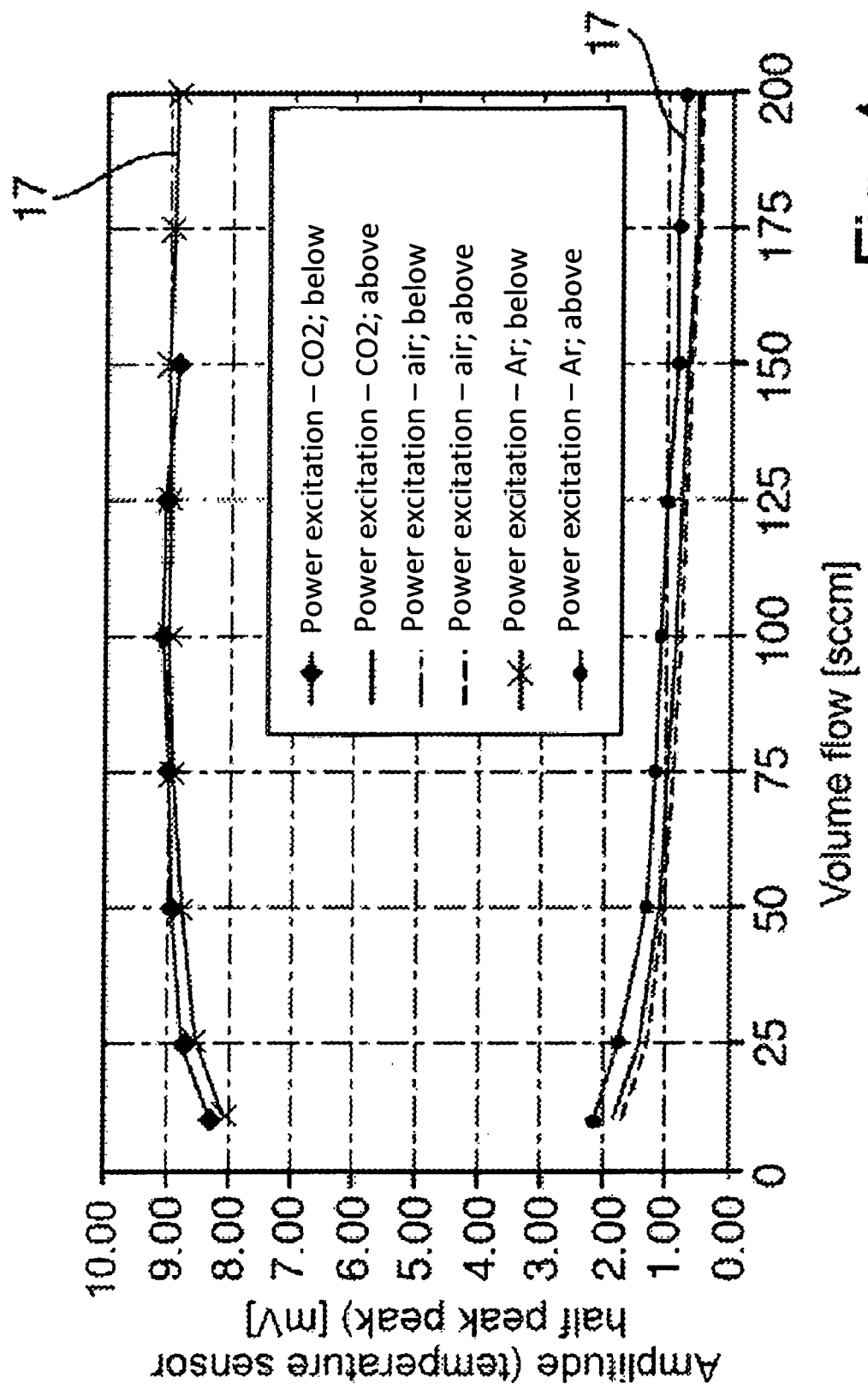

THERMAL FLOW SENSOR FOR DETERMINING A GAS OR THE COMPOSITION OF A GAS MIXTURE AS WELL AS ITS FLOW VELOCITY

TECHNICAL FIELD

The invention refers to a thermal flow sensor that serves to determine a gas or the composition of a gas mixture as well as its flow velocity.

BACKGROUND DISCUSSION

Thermal flow sensors are well-known from the current state of the art. Such sensors are, for example, used to determine the flow velocity of a gas. Since for physical reasons thermal flow sensors also react to thermal characteristics of the gas in which they are used in addition to the flow velocity, an exact or precise determination of the flow velocity is no longer possible when the thermal characteristics of the gas change. Such changes in the thermal characteristics may occur during the measuring operation of a flow sensor if, for example, the composition of a gas mixture or the gas itself changes.

This disadvantage is compensated by a recalibration of the thermal flow sensor used. This is typically done by introducing another sensor that identifies the gas present and/or the composition of the gas mixture instead of the flow velocity in order to thus determine the thermal characteristics of the gas and/or the gas mixture on which the determination of the flow velocity is based. However, for this purpose, as mentioned before, another sensor is required without which a recalibration would be impossible.

Alternatively, a recalibration may be obtained using a special software. The gas present or the composition of the gas mixture must be entered into the software for this purpose. It is therefore a disadvantage that another step from the operating staff, namely, a manual input, is required.

SUMMARY OF THE INVENTION

The object of this invention is therefore to propose a thermal flow sensor that shows increased user-friendliness.

This object is solved according to the invention by a thermal flow sensor and a flow meter.

With regard to the thermal flow sensor, the object is solved in such a way that the thermal flow sensor to determine a gas or the composition of a gas mixture and its flow velocity includes the following:

- a substrate onto which at least a first dielectric layer is applied;
- at least one heating structure that is applied onto the first dielectric layer and serves to heat the gas or the gas mixture;
- at least a first temperature sensor element that is applied onto the first dielectric layer at a distance from the heating structure and captures the temperature of the gas or gas mixture heated at the heating structure;
- a control device that controls the heating structure in a first operating mode in such a way that the heating structure shows a predetermined temperature, and controls the heating structure in a second operating mode in such a way that a power input into the heating structure corresponds to a predetermined power;
- an evaluation unit which determines at least one physical characteristic of the gas present or the gas mixture (2) on the basis of the operating modes and identifies the gas present or the composition of the gas mixture (2) as well as its flow velocity on the basis of this physical characteristic.

The object is further solved according to the invention by the thermal flow sensor determining the gas present or the composition of the gas mixture and simultaneously the flow velocity in dependence on the gas present or the composition of the gas mixture. For this purpose, the thermal flow sensor determines a physical characteristic, preferably the thermal conductivity of the gas or the gas mixture and uses it to determine the gas present or the gas mixture as well as its flow velocity.

Such thermal flow sensors have the advantage that incorrect measurements of the flow velocity due to a change in the gas or the composition of the gas mixture may be avoided since a change in the gas or the composition of the gas mixture also leads to a change in the thermal conductivity that is used to determine the gas present or the gas mixture.

For this purpose, the thermal flow sensor comprises a control device that can switch at least between two operating modes. In the second operating mode, the power input to the heating structure is consistently adjusted to a predetermined power to thus determine the gas present or the composition of a gas mixture. In the first operating mode, it adjusts the temperature of the heating structure on the basis of the determined gas present or the determined composition of a gas mixture in such a way that the heating structure demonstrates a predetermined temperature, so that the gas or gas mixture to be heated corresponds to a predetermined gas temperature at least in the area around the heating structure.

The control device controls the temperature of the heating structure in the first operating mode, e.g. with a DC voltage signal or an AC voltage signal in such a way that the heating structure shows a predetermined temperature. For a DC voltage signal, the set temperature may be adjusted directly through the DC voltage signal, whereas the set temperature may be adjusted via the average value of the AC voltage signal if an AC voltage signal is used.

The thermal flow sensor is thus self-calibrating thanks to the inference to the gas present or the gas mixture. In this way, an incorrect measuring of the flow velocity after a gas mixture change can be avoided.

One advantageous embodiment provides that the evaluation unit determines the composition of the gas mixture based on the measured thermal conductivity with regard to the concentration and that for a concentration determination of the composition of the gas mixture, the individual components of the gas mixture must be known to the evaluation unit. Due to the determination of the concentration of the composition of the gas mixture with an accuracy of 5%, the flow velocity may be determined up to 10% of the measuring value, preferably 5%.

The option of determining the concentration of the gas mixture present and the simultaneous determination of its flow velocity opens up further areas of application:

- such thermal flow sensors may, for example, be used in biogas plants to determine the volume fraction of methane in addition to the flow velocity which allows one to make conclusions regarding the fuel value of the gas.
- a simultaneous measurement of the flow velocity and the composition of a gas mixture is also advantageous in the field of medical engineering, e.g. for spirometers to monitor the functioning of the lungs and vital capacity.
- a simultaneous measurement of the air volume and the composition ($CO_2$ share) of the air flowing out of a room is also conceivable in the area of air-conditioning technology, in order to allow an optimized addition of fresh air.

Another advantageous embodiment provides that the substrate has a recess at least in the first area, so that the first dielectric layer develops a membrane at least in the first area on the substrate, and that at least one heating structure in the first area is arranged on the first dielectric layer developed into a membrane. The generation of a membrane and the arrangement of the heating structure on this membrane allows improved uncoupling of the heating structure from the rest of the sensor in terms of thermal technology, to thus allow a fast and precise measurement that is as sensitive as possible.

Another advantageous embodiment provides a second temperature sensor element being applied to the first dielectric layer. The embodiment especially provides a heating structure being arranged along a flow direction of the gas or the gas mixture between the first and the second temperature sensor elements. The embodiment further provides that the second temperature sensor element is made of a material that has a temperature coefficient of resistance in the range of 1 000-11 000 ppm/Kelvin, preferably in the range of 2 000-11 000 ppm/Kelvin, especially preferably in the range of 3 000-11 000 ppm/Kelvin.

Another advantageous embodiment provides that the heating structure and the first temperature sensor element are each made of a material that has a temperature coefficient of resistance in the range of 1 000-11 000 ppm/Kelvin, preferably in the range of 2 000-11 000 ppm/Kelvin, especially preferably in the range of 3 000-11 000 ppm/Kelvin. The embodiment especially provides that the heating structure is made of nickel or platinum. By developing the heating structure and the first temperature sensor element from one material each with an almost linear and/or a continuously increasing temperature coefficient of resistance, a temperature measurement directly on the heating structure becomes obsolete since this temperature can be calculated with the ohmic resistance of the heating structure and the known value of the temperature coefficient of the resistance and can thus be determined. Typically, the heating structure and the first temperature sensor element are made of the same material, preferably platinum. It is also conceivable that the heating structure is made of platinum and is the first temperature sensor element of nickel, thus both are made of different materials.

Another advantageous embodiment provides that the control device keeps the relation between power applied and the predetermined temperature mainly constant in a third operating mode. This allows the reduction of influences that interfere with the measuring result, such as temperature variations and pressure variations during the determination of the flow velocity.

Another advantageous embodiment provides that the control device accesses the heating structure with an excitation signal and the evaluation unit captures the temperature of the gas flowing past the first temperature sensor element and the second temperature sensor element with at least one first response signal and a second response signal, that the first response signal originates with the first temperature sensor element and the second response signal from the second temperature sensor element. The embodiment especially provides that the evaluation unit to determine the flow velocity compares the first and/or the second response signal with first reference values. It is further provided that the evaluation unit compares the first and/or second response signal with second reference values to determine the gas present or the composition of the gas mixture.

Another advantageous embodiment provides that the excitation signal is an AC voltage signal. This AC voltage signal serves to generate a phase shift between the excitation signal and the first and/or second response signal, that the evaluation unit determines the phase shift between the excitation signal and the first and/or second response signal. The evaluation unit especially conducts a check and/or verification of the gas determined previously or the composition of the gas mixture determined previously as well as its flow velocity. As an alternative to the monitoring and/or verification described above, it may be provided that the evaluation unit determines another physical characteristic of the gas present or the gas mixture on the basis of the phase shift. The additional physical characteristic is especially the temperature conductivity of the gas present or the gas mixture. As an alternative to the temperature conductivity, the thermal conductivity, the specific thermal capacity, the density as well as the dynamic or kinematic viscosity may be identified.

Another advantageous embodiment provides that the first dielectric layer and/or the second dielectric layer shows a layer thickness of less than 100 microns, preferably less than 50 microns, especially preferably less than 15 microns. The layer thickness both for the first dielectric layer and the second dielectric layer is a compromise between mechanical stability and the thermal transfer through those layers.

Another advantageous embodiment provides that the first and the second dielectric layer are made of the same material. Preferably the first and second dielectric layer are made of a polymer.

With regard to the flow meter, the object is solved with a flow meter with a thermal flow sensor according to at least one of the above-described embodiments.

BRIEF DESCRIPTION OF THE DRAWINGS

The invention is further illustrated referring to the following drawings. Illustrated are:

FIG. 4: a second measuring curve comprising the second reference values.

DETAILED DISCUSSION IN CONJUNCTION WITH THE DRAWINGS

Figure 1:
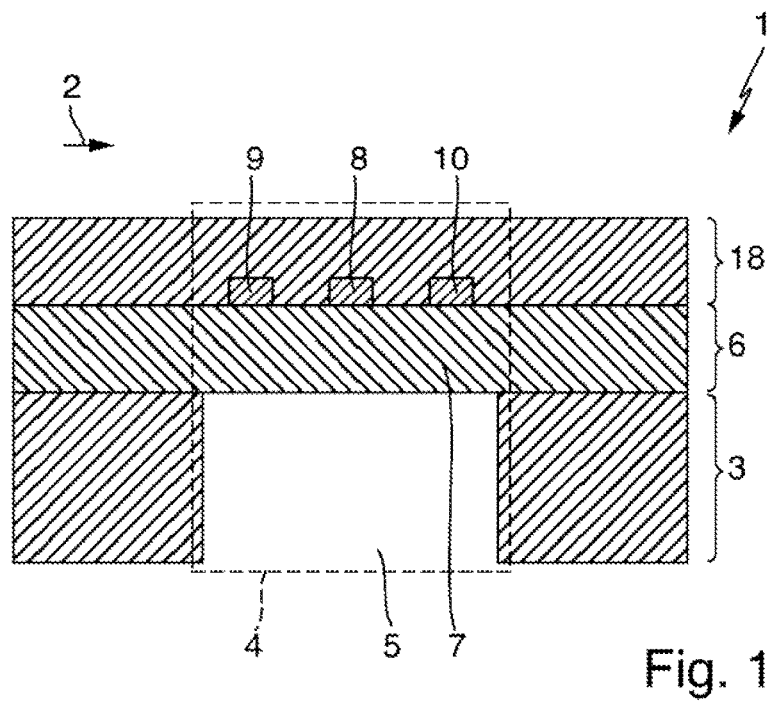
FIG. 1: a cross-section of an embodiment of the flow sensor according to the invention.

FIG. 1 shows a cross-section of an embodiment of the flow sensor 1 according to the invention. The thermal flow sensor 1 features a substrate 3 onto which a first dielectric layer 6 is applied. The substrate 3 further features a recess 5 in a first area 4 so that the first dielectric layer generates a membrane 7 in the first area 4 on the substrate 3. A heating structure 8 is applied onto the membrane 7 in such a way that it is between a first and second temperature sensor element 9, 10 along the flow direction of the gas or the gas mixture 2 and serves to heat the gas or gas mixture 2. The two temperature sensor elements 9, 10 are also applied onto the first dielectric layers 6 and preferably arranged in such a way that they are in the first area 4. Those two temperature sensor elements 9, 10 serve to capture the temperature of the gas or gas mixture 2 heated at the heating structure 8. In order to protect the heating structure 8 and the two temperature sensor elements 9, 10, a second dielectric layer 16 is applied onto the first dielectric layer 6. In order to determine a gas or the composition of a gas mixture 2, the side of the second dielectric layer 18 that is pointing away from the substrate 3 is exposed to the flowing gas or gas mixture 2.

The thermal flow sensor 1 further comprises a control device 11 that controls the heating structure 8 with an excitation signal 12 and controls it in a first operating mode in such a way that the heating structure has a predetermined temperature and controls the heating structure 8 in a second operating mode such a way that a power input into the heating structure 8 is mainly adjusted to a predetermined power. Thus, the control devices uses the heating structure to control the gas temperature of the gas or the gas mixture to the predetermined temperature in the first operating mode. In the second operating mode, the control device controls the power input into the heating structure mainly to a predetermined power that is typically constant at least in its average value. The excitation signal 13 is an AC voltage signal that has, for example, an excitation frequency of 1 Hz. It has been proven as advantageous if the temperature predetermined in the first operating mode shows a constant overtemperature of the gas and/or gas mixture compared to the surrounding temperature in the range of 120° C. and the power predetermined in the second operating mode has a peak-peak value of 20 mW (milliwatts). The excitation frequency, the predetermined temperature and the peak-peak value of the AC voltage signal may vary depending on the gas present and/or the gas mixture 2. In addition to a first and a second operating mode, the control device 11 keeps the relationship between the power input and the predetermined temperature mainly constant in a third operating mode.

Furthermore, the control device 11 is designed as a switchable device so it can be switched from one operating mode to another.

In addition to the control device 11, the thermal flow sensor 1 also has an evaluation unit 12 which determines at least the gas present or the composition of the gas mixture 2 as well as the flow velocity of the gas and/or the gas mixture by means of the different operating modes. For this purpose, the thermal flow sensor measures the thermal conductivity of the gas or the gas mixtures and identifies the gas present and/or the composition of the gas mixture on the basis of the thermal conductivity. For this purpose, the evaluation unit 12 captures the temperature of the gas and/or gas mixtures 2 passing the first temperature sensor element 9 by means of a first response signal 14 and the temperature of the gas and/or gas mixture 2 passing the second temperature sensor element 10 by means of a second response signal 15. In order to determine the flow velocity, the evaluation unit 12 either separately compares the first response signal 14 with a first reference value 16 or the second response signal 15 with a first reference value 16, or the first and second response signal 14, 15 together with the first reference values 16. In order to determine the gas present or the composition of the gas mixture 2, the evaluation unit 12 either compares the first response signal 14 with second reference values 17 or the second response signal 15 with the second reference values 17, or the first and the second response signal 14, 15 with the second reference values 17, with the first reference values 16 being different from the second reference values 17. In order to determine the composition of the gas mixtures 2 which is preferably a binary gas mixture, such as, for example, an mixture of argon an helium, the evaluation unit 12 has to know the individual components, in this case helium and argon in order to be able to determine the concentration and composition of the (binary) gas mixture.

Figures 2A, 2B:
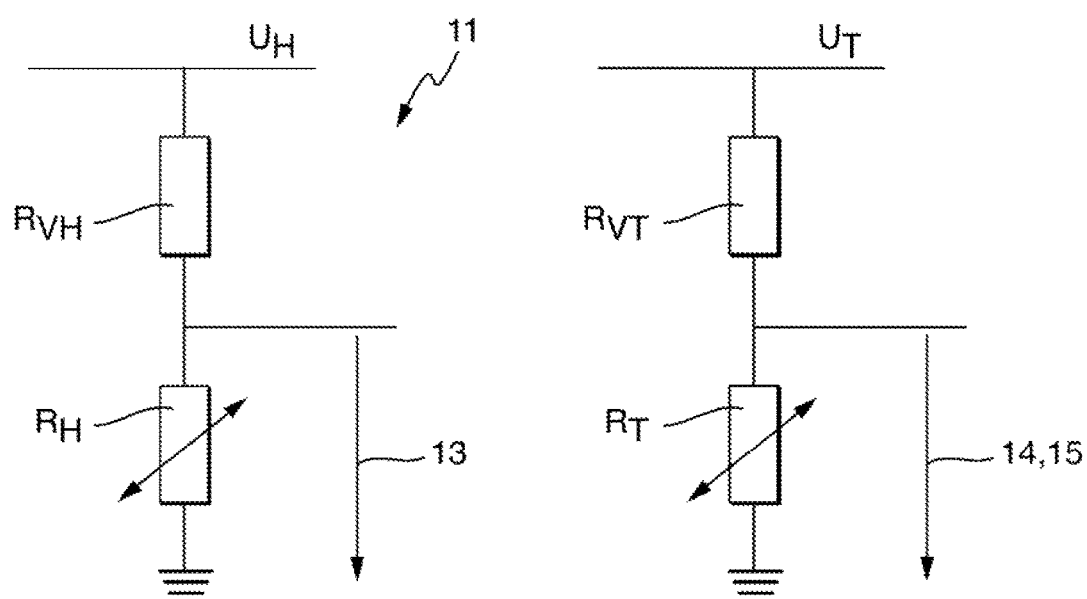
FIG. 2: an electrical diagram of the control device and a voltage divider that serves to capture a response signal.

FIG. 2a) shows and electrical diagram of the control device 11 and FIG. 2b) a voltage divider that serves to capture the response signals 14, 15. The control device 11 in its most simple form is a voltage divider, with the ohmic heat resistance of the heating structure 8 being represented by $R_H$ and a series resistor $R_{VH}$ for the heat structure 8 being inserted before the heat resistor. By means of the total voltage for the heating structure UH it is thus possible to generate the excitation signal 13 which is, as mentioned above, an AC voltage signal with a peak-peak value of 20 mW. The excitation signal 13 to be used may either be a sine-wave voltage, a square-wave voltage or any other form of an AC voltage signal.

FIG. 2b) shows a voltage divider to capture a response signal 14, 15. For simplicity's sake, FIG. 2b) only shows the voltage divider that serves to capture the first response signal 14 of the first temperature sensor element 9. The evaluation unit 12 therefore in its most simple case comprises at least one voltage divider for teach temperature sensor element 9, 10. In FIG. 2b), the ohmic resistance of the temperature sensor element is represented as $R_T$. The voltage divider further comprises a series resistor $R_{VT}$ and is operated with a total voltage $U_T$, with the total voltage $U_T$ being a direct current. The first response signal 14 is tapped above the resistor of the temperature sensor element $R_T$.

Figure 3:
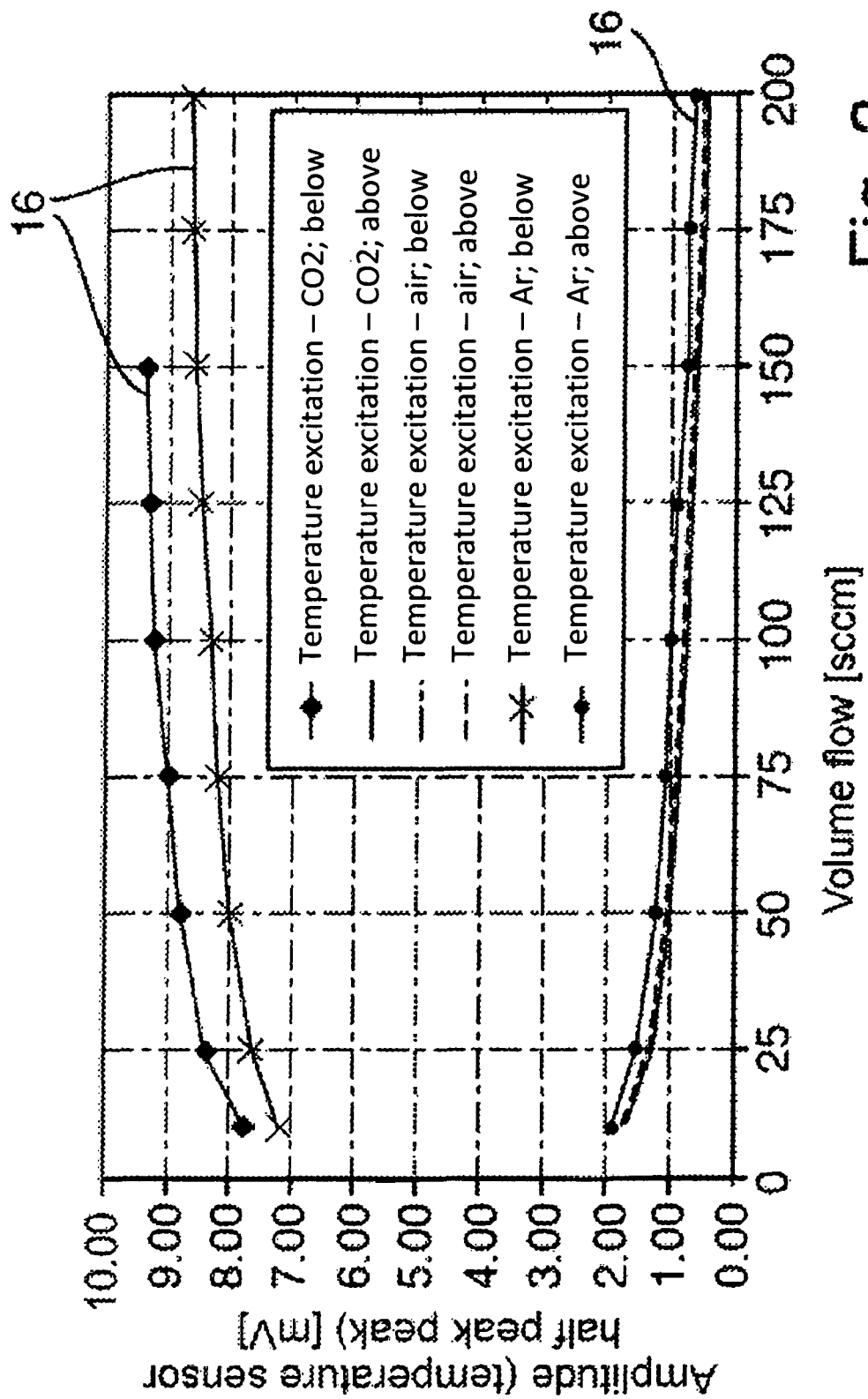
FIG. 3: a first measuring curve comprising the first reference values

FIG. 3 shows a first measuring curve that comprises the first reference values 16 required for the determination of the flow velocity of the gas or the gas mixture 2.

FIG. 4 shows a second measuring curve that allows the determination of the gas present or the composition of the gas mixture 2.

The invention claimed is:

1. A thermal flow sensor configured for determining a gas or the composition of a gas mixture as well as its flow velocity, comprising:
    a substrate onto which at least one dielectric layer is applied;
    at least one heating structure that is applied onto said at least one dielectric layer and serves to heat the gas or the gas mixture;
    at least one temperature sensor element that is applied onto said at least one dielectric layer at a distance from said at least one heating structure and captures the temperature of the gas or gas mixture heated at said at least one heating structure;
    a control device that controls said at least one heating structure in a first operating mode in such a way that said at least one heating structure shows a predetermined temperature, and controls said at least one heating structure in a second operating mode in such a way that a power input into said at least one heating structure corresponds to a predetermined power; and
    an evaluation unit which determines at least one physical characteristic of the gas present or the gas mixture on the basis of said operating modes and determines the gas present or the composition of the gas mixture as well as its flow velocity on the basis of this physical characteristic.

2. The thermal flow sensor according to claim 1, wherein:
    said evaluation unit identifies the concentration of the composition of the gas mixture; and
    the individual components of the gas mixture is necessarily communicated to said evaluation unit in order to determine the concentration of the composition of the gas mixture.

3. The thermal flow sensor according to claim 1, wherein:
said substrate has a recess at least in a first area, so that said at least one first dielectric layer forms a membrane at least in said area on said substrate; and
said at least one heating structure in said first area is arranged on said at least one dielectric layer formed into said membrane.

4. The thermal flow sensor according to claim 1, said at least one temperature sensor further comprises:
a second temperature sensor element which is applied to said at least one dielectric layer.

5. The thermal flow sensor according to claim 4, wherein:
said at least one heating structure is arranged along a flow direction of the gas or the gas mixture between said at least one first and said second temperature sensor elements.

6. The thermal flow sensor according to claim 5, wherein:
said second temperature sensor element is made of a material that has a temperature coefficient of resistance in the range of 1 000-11 000 ppm/Kelvin.

7. The thermal flow sensor according to claim 1, wherein:
said at least one heating structure and said at least one first temperature sensor element are each made of a material that has a temperature coefficient of resistance in the range of 1 000-11 000 ppm/Kelvin.

8. The thermal flow sensor according to claim 1, wherein:
said control device keeps the relation between the predetermined power and the predetermined temperature constant in a third operating mode.

9. The thermal flow sensor according to claim 8, wherein:
said control device controls said at least one heating structure with an excitation signal and said evaluation unit captures the temperature of the gas flowing past said first temperature sensor element and a second temperature sensor element by means of at least one response signal and a second response signal.

10. The thermal flow sensor according to claim 9, wherein:
said evaluation unit configured to determine the flow velocity compares said first and/or said second response signal with first reference values or with second reference values.

11. The thermal flow sensor according to claim 9, wherein:
said excitation signal represents an AC voltage signal.

12. The thermal flow sensor according to claim 11, wherein:
said evaluation unit determines a phase shift between the excitation signal and said first and/or said second response signal.

13. The thermal flow sensor according to claim 12, wherein:
said evaluation unit conducts a verification of the determination of the gas or the composition of the gas mixture as well as its flow velocity on the basis of the phase shift.

14. The thermal flow sensor according to claim 12, wherein:
said evaluation unit determines a further physical characteristic of the gas present or the gas mixture based on the phase shift.

15. The thermal flow sensor according to claim 1, wherein:
said thermal flow sensor comprises a second dielectric layer;
said first dielectric layer and/or a second dielectric layer show a layer thickness of less than 100 microns.

16. The thermal flow sensor according to claim 15, wherein:
said first and said second dielectric layers are of the same material.

17. The thermal flow sensor according to claim 16, wherein:
said first and the second dielectric layers are made of a polymer.

18. A flow meter with a thermal flow sensor, comprising:
a thermal flow sensor configured for determining a gas or the composition of a gas mixture as well as its flow velocity, comprising: a substrate onto which at least one dielectric layer is applied; at least one heating structure that is applied onto said at least one dielectric layer and serves to heat the gas or the gas mixture; at least one temperature sensor element that is applied onto said at least one dielectric layer at a distance from said at least one heating structure and captures the temperature of the gas or gas mixture heated at said at least one heating structure; a control device that controls said at least one heating structure in a first operating mode in such a way that said at least one heating structure shows a predetermined temperature, and controls said at least one heating structure in a second operating mode in such a way that a power input into said at least one heating structure corresponds to a predetermined power; and an evaluation unit which determines at least one physical characteristic of the gas present or the gas mixture on the basis of said operating modes and determines the gas present or the composition of the gas mixture as well as its flow velocity on the basis of this physical characteristic.

* * * * *